US005505205A

United States Patent [19]

Solomon et al.

[11] Patent Number: 5,505,205

[45] Date of Patent: Apr. 9, 1996

[54] INTERFACE ELEMENT FOR MEDICAL ULTRASOUND TRANSDUCER

[75] Inventors: Rodney J. Solomon, Andover, Mass.; Gregory G. Vogel, Londonderry, N.H.; Robert W. King, Lexington; Susan Williams, Tyngsboro, both of Mass.

[73] Assignee: Hewlett-Packard Company, Palo Alto, Calif.

[21] Appl. No.: 275,562

[22] Filed: Jul. 15, 1994

Related U.S. Application Data

[63] Continuation-in-part of Ser. No. 2,306, Jan. 8, 1993, abandoned.

[51] Int. Cl.$^{6}$ .......... A61B 8/00

[52] U.S. Cl. .......... 128/662.03; 128/663.01

[58] Field of Search .......... 128/662.03–662.06, 128/663.01; 73/625–626; 310/334, 324; 526/264

[56] References Cited

U.S. PATENT DOCUMENTS

| | | | |
|---|---|---|---|
| 2,922,807 | 1/1960 | Merker | 260/448.2 |
| 2,956,044 | 10/1960 | Merker | 260/46.5 |
| 3,203,919 | 8/1965 | Brachman | 260/29.6 |
| 3,228,741 | 1/1966 | Becker | 351/160 |
| 3,431,046 | 3/1969 | Conrad et al. | 351/160 |
| 4,152,508 | 5/1979 | Ellis et al. | 526/279 |
| 4,248,989 | 2/1981 | Novicky | 526/264 |
| 4,387,720 | 6/1983 | Miller | 128/663.01 |
| 4,391,281 | 7/1983 | Green | 128/660 |
| 4,424,328 | 1/1984 | Ellis | 526/279 |
| 4,437,032 | 3/1984 | Gelhard | 310/324 |
| 4,463,149 | 7/1984 | Ellis | 526/279 |
| 4,518,992 | 5/1985 | Kessler et al. | 358/112 |
| 4,550,609 | 11/1985 | Johnson | 73/642 |
| 4,587,972 | 5/1986 | Morantte, Jr. | 128/660 |
| 4,604,479 | 8/1986 | Ellis | 556/440 |
| 4,625,007 | 11/1986 | Ellis et al. | 526/279 |
| 4,686,267 | 8/1987 | Ellis et al. | 526/245 |
| 4,699,150 | 10/1987 | Kawabuchi et al. | 128/663.01 X |
| 4,826,889 | 5/1989 | Ellis et al. | 522/99 |
| 4,826,936 | 5/1989 | Ellis | 526/258 |
| 4,996,275 | 2/1991 | Ellis et al. | 526/245 |
| 5,032,658 | 7/1991 | Baron et al. | 526/321 |
| 5,127,410 | 7/1992 | King et al. | 128/662.03 |
| 5,327,895 | 7/1994 | Hashimoto et al. | 128/662.03 |

FOREIGN PATENT DOCUMENTS

| | | |
|---|---|---|
| 489222A3 | 6/1992 | European Pat. Off. . |
| 2377134 | of 1978 | France . |
| 2-297347 | 2/1991 | Japan . |

OTHER PUBLICATIONS

IEEE Transactions on Sonics and Ultrasonics, May 1985, vol. SU–32, No. 3.

Modern Plastics, Mid–Oct. Issue 1988, vol. 65, No. 11, p. 20.

*Primary Examiner*—Francis Jaworski

[57] ABSTRACT

An ultrasound transducer assembly includes an ultrasound transducer for transmitting and receiving ultrasound energy and one or more interface elements for conducting transmitted ultrasound energy from the transducer to a patient's body and for conducting received ultrasound energy from the patient's body to the transducer. At least one ultrasound-transmissive interface element is fabricated of a polymeric material. The material preferably has a sound speed that approximately matches the speed of sound in human tissue. The material comprises at least one primary rigid component material and at least one secondary component material, and has a Shore D durometer hardness value of greater than about 60D, and a sound speed of between about 1,450 meters/second and about 1,700 meters/second. The ultrasound-transmissive element fabricated of a polymeric material can be a protective lens cover, an ultrasound lens or lens element, an ultrasound-transmissive window or a sound pipe.

20 Claims, 3 Drawing Sheets

INTERFACE ELEMENT FOR MEDICAL ULTRASOUND TRANSDUCER

This application is a continuation-in-part of U.S. application Ser. No. 08/002,306, filed Jan. 8, 1993 and now abandoned.

FIELD OF THE INVENTION

This invention relates to transducer assemblies for medical ultrasound systems and, more particularly, to an interface element for coupling ultrasound energy between a transducer and a patient's body.

BACKGROUND OF THE INVENTION

Ultrasound transducers are frequently utilized in a variety of medical applications. The transducer may include a single element or an array of transducer elements. The transducer is typically part of an ultrasound imaging system for generating an image of a region of interest within a patient's body. For many applications, the transducer is mounted in a hand-held probe which is positioned adjacent to a selected external area of the patient's body, for example, adjacent to the chest wall to scan the heart. In other instances, the transducer is mounted in a probe that can be positioned in an internal body cavity or passage. The transducer frequently includes an ultrasound lens for focusing the ultrasound energy.

When an ultrasound transducer is used for medical imaging, it is extremely important to ensure that any materials between the transducer and the region of the patient's body being imaged do not distort or otherwise interfere with the image. In particular, when the ultrasound energy encounters an interface between materials having different sound speeds and acoustic impedances the energy can be partially reflected and refracted. Since the speed of sound in air (about 332 meters/second) is much different from the speed of sound in the human body (about 1540 meters/second) and their impedances are significantly different, it is important to eliminate air between the ultrasound transducer and the patient's body. For this reason, it is common practice to employ an acoustic gel between the transducer and the patient's body.

Single piece ultrasound lenses for flat piezoelectric crystals typically have an outer structure that is convex. This permits the transducer to better contact the body portion being imaged, and provides a lens for focusing ultrasound energy. In order to provide a lens for focusing ultrasound energy that is planar on the inside surface that contacts the transducer and convex on the outside, the sound speed of the material must be lower than the sound speed within the body. A typical material that has such a low sound speed is silicone rubber, which is relatively soft, is not durable, is quite attenuative and must be cast in place over the ultrasound transducer. It would be desirable to provide a protective cover over the silicone rubber lens. However, the cover must not significantly distort the ultrasound image or attenuate the ultrasound energy.

Another ultrasound transducer configuration involves the use of a rotating transducer and lens in a transesophageal probe as described in U.S. Pat. No. 5,127,410 issued Jul. 7, 1992. The transducer and lens are positioned behind a sealed window and rotate relative to the window. The lens includes a silicone rubber inner element and a urethane rubber outer element. A lubricant fills a gap between the surfaces of the lens and the window. The urethane rubber lens element is relatively soft and may not provide adequate mechanical support for the window in the event that an object presses or impacts against the window.

SUMMARY OF THE INVENTION

According to the present invention, a medical ultrasound transducer assembly is provided. The transducer assembly comprises an ultrasound transducer for transmitting and receiving ultrasound energy and interface means for conducting transmitted ultrasound energy from the transducer to a patient's body and for conducting received ultrasound energy from the patient's body to the transducer. The interface means comprises at least one ultrasound-transmissive element which is fabricated of a polymeric material. The polymeric material may comprise at least one primary rigid component and at least one secondary component material, and has a Shore D durometer hardness value of greater than about 60 D and a sound speed of between about 1,450 meters/second and about 1,700 meters/second. The ultrasound transducer can comprise a single transducer element or an array of transducer elements.

The polymeric materials of the invention are relatively hard and durable and can be machined or cast into desired shapes. The sound speed in the polymeric materials approximately matches the speed of sound and the impedance of the soft tissues in the human body so that distortion of the ultrasound image and reflection of ultrasound energy are minimized.

In a first embodiment of the invention, the interface means includes an ultrasound lens, and the ultrasound-transmissive element comprises a protective cover on the ultrasound lens. The protective cover is in contact with the patient's body during use of the transducer.

In a second embodiment, the transducer assembly includes a fixed window and means for rotating the transducer relative to the fixed window. An ultrasound lens is affixed to and rotates with the transducer. The ultrasound-transmissive element comprises an inner protective cover fabricated of a polymeric material affixed to the ultrasound lens and located between the ultrasound lens and the window.

In a third embodiment, the transducer assembly includes a fixed window and means for rotating the transducer relative to the fixed window. The window is fabricated of a polymeric material.

In a fourth embodiment, the transducer assembly includes a fixed window and means for rotating the transducer relative to the fixed window. An ultrasound lens is affixed to and rotates with the transducer. The ultrasound-transmissive element comprises an outer element of the ultrasound lens fabricated of a polymeric material.

In a fifth embodiment, the ultrasound-transmissive element fabricated of a polymeric material, comprises a sound pipe for coupling ultrasound energy between the transducer and the patient's body. The sound pipe can comprise a standoff for spacing the transducer from the patient's body. Alternatively, the sound pipe can include a surface for changing the direction of propagation of ultrasound energy by total internal reflection within the sound pipe.

BRIEF DESCRIPTION OF THE DRAWINGS

For better understanding of the present invention, reference is made to the accompanying drawings which are incorporated herein by reference and in which.

DETAILED DESCRIPTION

Figure 1:
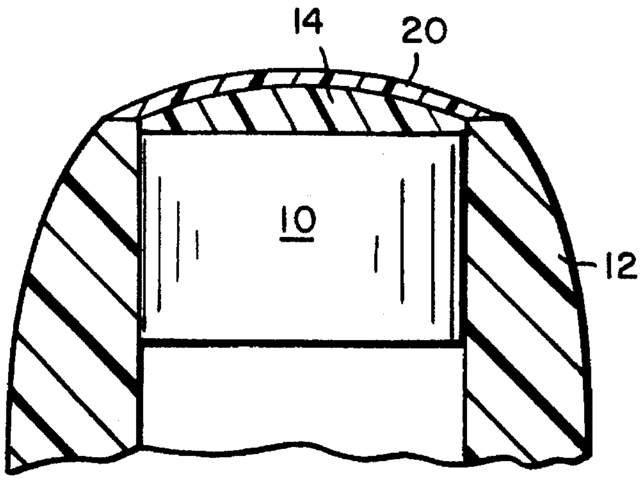
FIG. 1 is a partial cross-sectional view of a transducer assembly including a soft ultrasound lens and a protective cover of a polymeric material in accordance with the invention.

The present invention provides a novel interface element for use between an ultrasound transducer and a patient's body. The invention is based on the discovery that certain rigid compounds have properties that closely match those of the human body in the transmission of ultrasound energy. The materials are used to fabricate various ultrasound-transmissive elements that are positioned between an ultrasound transducer and a patient's body.

The most important requirements for such an ultrasound-transmissive element are the speed of sound in the material, its acoustic impedance, and its hardness. Preferably, the material has a sound speed between about 1,450 meters/second and about 1,700 meters/second, and an impedance of between about 1.5 and about 1.7 Mrayls. This ensures that the ultrasound image will not be significantly distorted or otherwise degraded when the transmitted or received ultrasound energy passes through the element. Most preferably, the speed of sound within the material preferably approximately matches the speed of sound in soft tissues in the human body (approximately 1,540 meters/second). It has been found that to have adequate machinability, to allow formation of a wide variety of shapes and sizes of the element, the material should have a Shore D durometer hardness value greater than about 60. As is known to those skilled in the art, a standard technique used to determine Shore D durometer hardness values is provided by ASTM Test No. 2240-91.

As noted above, a further requirement of the ultrasound-transmissive element is that the acoustic impedance of the rigid material should be approximately matched to the acoustic impedance of the human body (1.54 Mrayls). Acoustic impedances in a range of about 1.5 to 1.7 Mrayls are considered acceptable.

It has been found that there is a correlation between the physical and acoustic properties of most homopolymeric materials; materials which are soft and flexible generally exhibit a slower speed of sound in the ultrasound frequency range (2.0–10.0 MHz). For example, soft materials, such as silicone rubbers having Shore D durometer hardness values of between about 45 and 50, have relatively low sound speeds of between about 1,000 and 1,300 meters/second. Conversely, harder materials, such as epoxy and acrylic plastics having Shore D hardness values of about 90, have relatively high sound speeds of between about 2,600 and 2,700 meters/second, and impedances of between about 2.6 and 2.8 Mrayls, well above the range that is acceptable for transmission of ultrasound energy to or from the human body.

A rigid, low sound speed material having the above preferred characteristics is Equalens® II contact lens material, available from Polymer Technology Corporation, Wilmington, Mass. It is noted, however, that although this material can be used to fabricate an ultrasound-transmissive element that can be positioned between an ultrasound transducer and a patient's body, it is relatively expensive. In addition, these materials often include a variety of additives used to provide characteristics such as wettability and gas permeability, which are typically required for contact lenses but are not required for the present ultrasound-transmissive elements.

In general, the rigid low sound speed materials used to fabricate the ultrasound-transmissive elements of the present invention have a composition including a silicone acrylic component, and a second, more rigid acrylic to increase hardness. By polymerizing these materials, for example into a copolymer, in various ratios, the hardness and sound speed can be adjusted to the respective desired ranges. The polymeric material for use as an ultrasound-transmissive element should also have good mechanical properties, allowing the material to be easily machined.

The secondary component generally can include any compound(s) from the family of methacrylates, such as t-butyl methacrylate, methacrylic acid, and the like, and/or styrenes, such as tertbutylstyrene. The primary rigid component generally can include any compound(s) from the family of siloxanes, such as tris(trimethylsiloxy)methacryloxypropylsilane (TRIS), bis(methacryloxypropyl)tetrakis(trimethylsiloxy)disiloxane (BIS), and the like. Preferably, the secondary component is a methacrylate due to its mechanical strength, hardness, and machinability. The methacrylates are generally more chemically robust than the styrenes, the latter having lower density, strength, chemical resistance. The preferred primary component is TRIS due to its acoustic properties (sound speed) and mechanical strength.

A first embodiment of an of the ultrasound-transmissive element fabricated of a rigid, low sound speed material is illustrated in FIG. 1. An ultrasound transducer 10 is mounted within a probe housing 12. The transducer 10 includes an array of transducer elements in a direction perpendicular to the plane of FIG. 1. The transducer 10 may include a matching layer as known in the art. An ultrasound lens 14 has a flat surface attached to transducer 10 and a convex outer surface. The convex outer surface of lens 14 is cylindrical in a direction perpendicular to the plane of FIG. 1. The lens 14 is typically fabricated of a soft material having a low sound speed, such as silicone rubber. A protective cover 20 fabricated of a rigid, low sound speed material, as described above, covers the convex outer surface of lens 14. The cover 20 has a shape that matches the outer surface of lens 14 to avoid any air gaps between these elements, since the lens material is cast onto the outer cover, excluding air. The cover 20 may typically have a thickness of about 0.5 millimeter. However, it will be understood that other thicknesses can be utilized. The cover 20 prevents damage to ultrasound lens 14 and does not distort or otherwise interfere with the ultrasound image obtained. The protective cover 20 is typically placed in contact with a patient's body using acoustic gel.

Figure 2A:
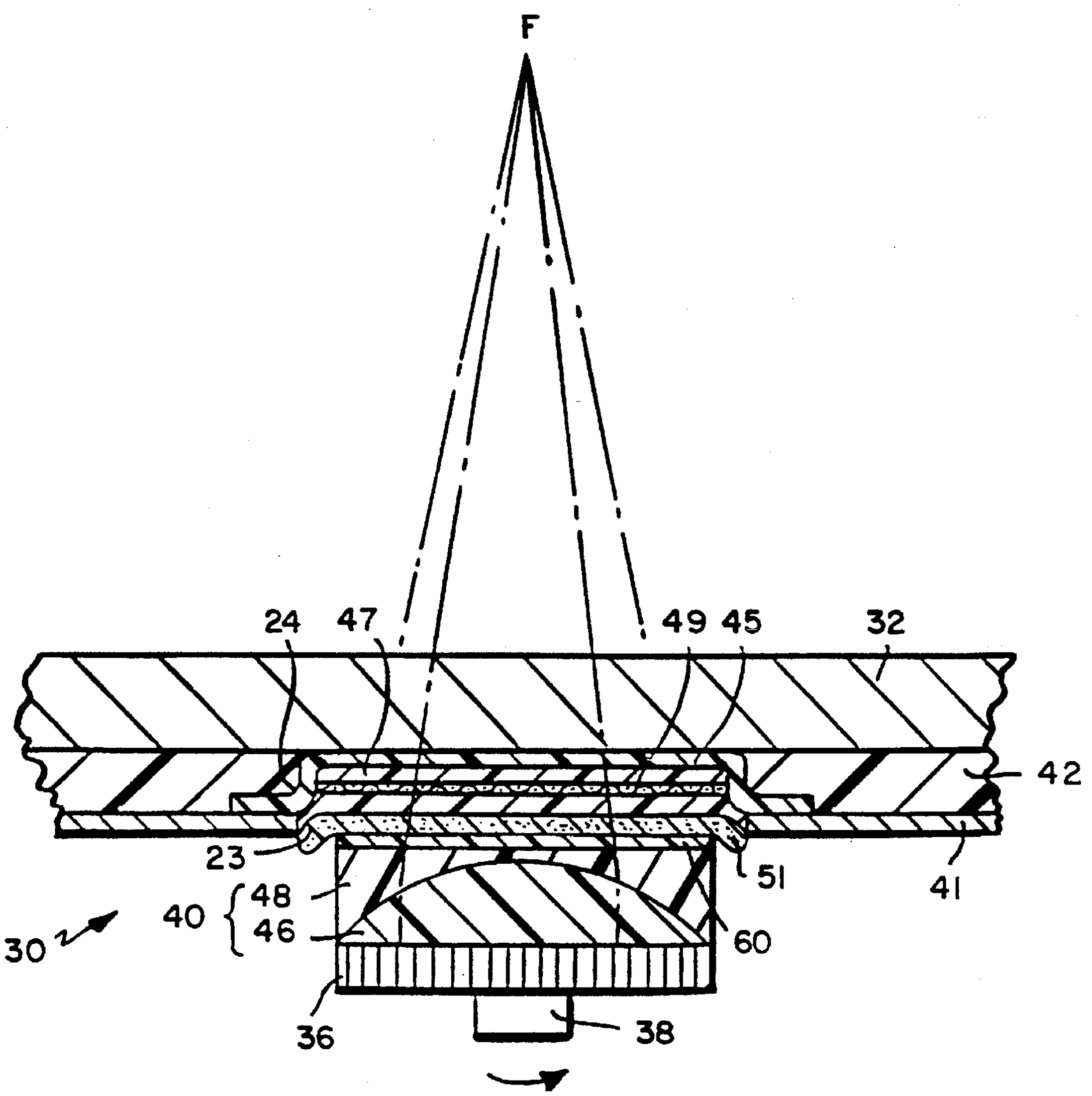
FIGS. 2A and 2B are cross-sectional views of transducer assemblies that employ a rotating transducer and lens.

Further embodiments of the ultrasound-transmissive element fabricated of rigid, low sound speed material are described with reference to FIG. 2A. An ultrasound transducer probe 30 is located in contact with a patient's body 32. The probe 30 includes a phased array ultrasound transducer 36 formed of piezoelectric material. Transducer 36 is rotated by a mechanism 38 which either directly or indirectly rotates the transducer utilizing a reciprocating motor or other suitable means. A compound lens 40 includes a convex cylindrical lens element 46 and a concave element 48 which mates to convex element 46. Lens element 46 is typically a silicone rubber such as RTV. The lens element 48 is typically fabricated of urethane rubber. A window assembly is mounted in a housing 41 covered by an epoxy seal 42. The window assembly includes a thin polyester film window 45 and a backing layer 47. The backing layer 47 may be fabricated of urethane rubber. The backing layer 47 may include an RFI screen 49. An acoustic lubricant 51, such as a fluorosilicone oil, is located between lens 40 and backing layer 47 to permit rotation of the transducer 36 and lens 40 relative to the window assembly. The probe assembly is described in more detail in U.S. Pat. No. 5,127,410, which is hereby incorporated by reference.

In accordance with a second embodiment of the invention, a protective cover 60 fabricated of a rigid, low sound speed material is affixed to the outer surface of lens element 48. The protective cover 60 prevents physical damage to the soft urethane lens element 48 as the transducer rotates. Furthermore, the cover 60 protects the urethane lens element 48 against degradation by the acoustic lubricant 51. Finally, the cover 60 provides a mechanical backing for the window assembly, thus reducing the possibility of damage to the window by pressure or impact from an external object.

Preferably, the cover 60 is compatible with the acoustic lubricant 51 to ensure that the acoustic lubricant 51 remains in place and does not evaporate or form air pockets during rotation of the lens 40.

In a third embodiment of the invention, the window 45 of transducer probe 30 is fabricated of a rigid, low sound speed material. In the prior art transducer assembly, the window 45 was very thin to reduce refraction and reflection of ultrasound energy, and the backing layer 47 was fabricated of urethane rubber. Thus the window assembly was subject to damage by an external object. By contrast, when the window 45 is fabricated of a rigid, low sound speed material, it can be made relatively thick since the acoustic properties are closely matched to those of the human body. Therefore, the potential for damage to the probe assembly is reduced without adversely affecting the ultrasound image. It will be understood that the protective cover 60 and the rigid, low sound speed window 45 can be used separately or in combination in the transducer assembly of FIG. 2.

Figure 2B:
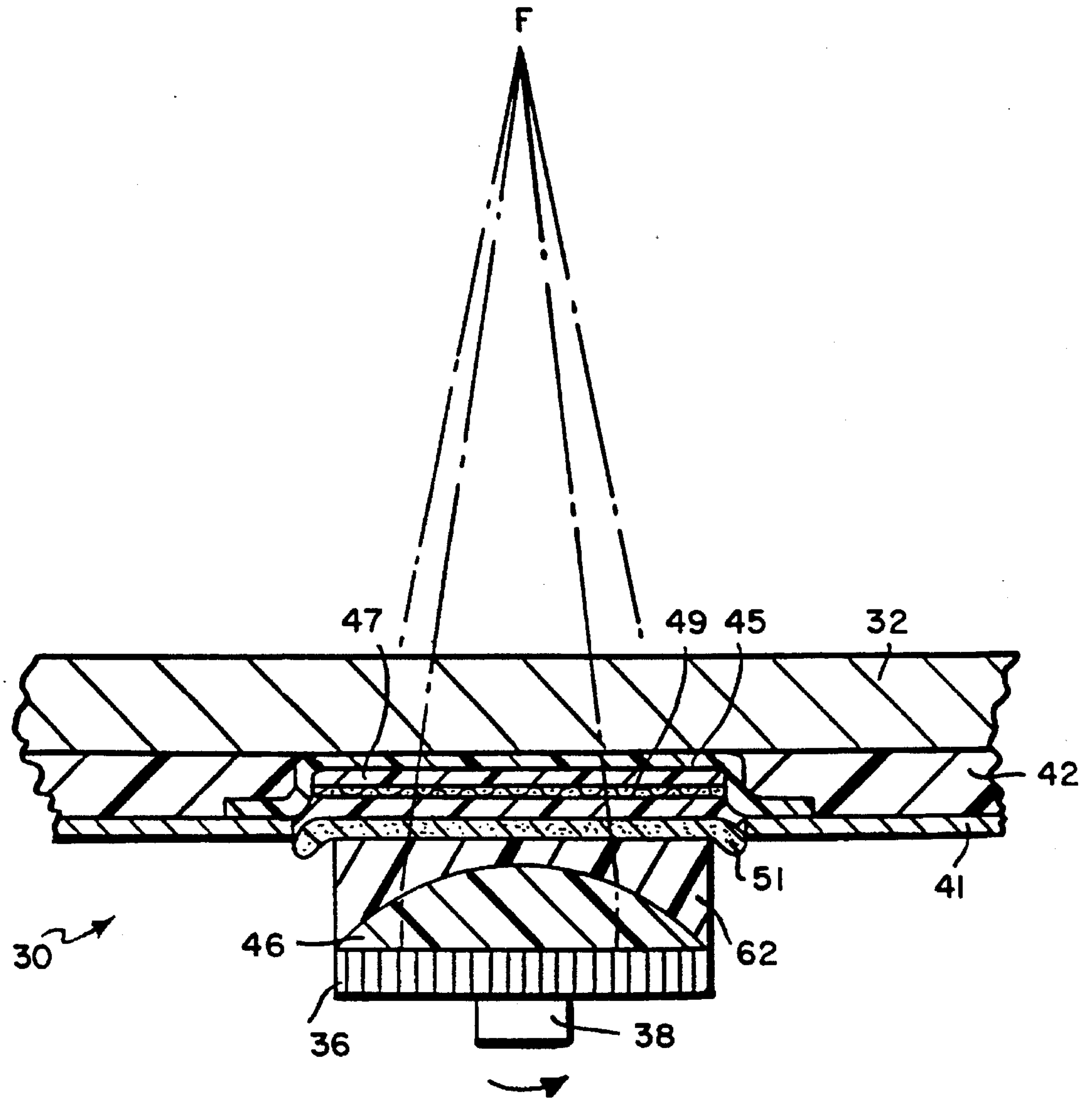

A fourth embodiment of the invention is shown in FIG. 2B. The ultrasound transducer probe 30 of FIG. 2B has a construction similar to the probe shown in FIG. 2A. Like elements in FIGS. 2A and 2B have the same reference numerals. In the embodiment of FIG. 2B, a lens element 62 which mates to convex lens element 46 is fabricated of a rigid, low sound speed material in accordance with the present invention. The lens element 62 provides similar advantages to the protective cover 60 shown in FIG. 2A and described above. The lens element 62 prevents physical damage to the convex element 46 and is not degraded by the acoustic lubricant 51. In addition, the lens element 62 of a rigid, low sound speed material provides a mechanical backing for the window assembly, thus reducing the possibility of damage to the window.

Figure 3:
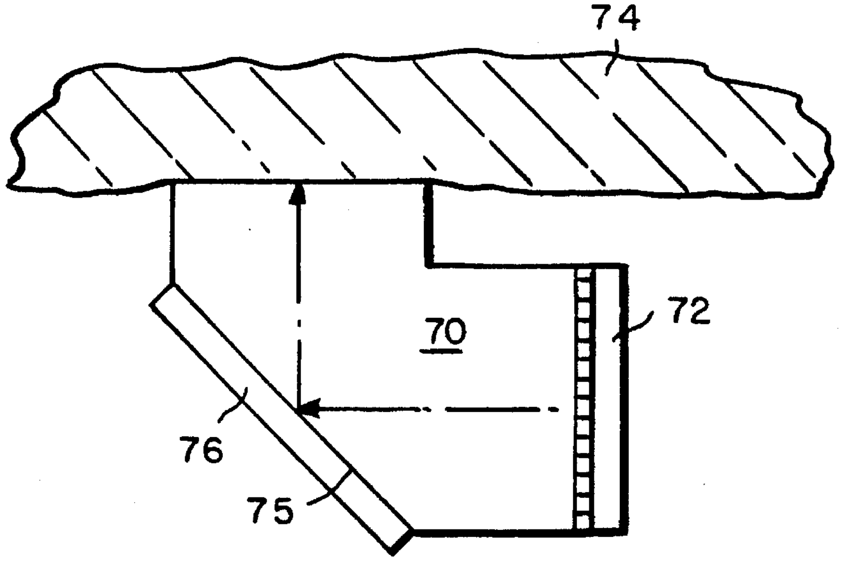
FIG. 3 is a schematic diagram of a transducer assembly that employs a sound pipe for coupling ultrasound energy between a transducer and a patient's body.

A fifth embodiment of the invention is illustrated in FIG. 3. A sound pipe 70 is used to transmit ultrasound energy between an ultrasound transducer 72 and a patient's body 74. The sound pipe is fabricated of a rigid, low sound speed material and is configured to change the direction of the ultrasound energy transmitted and received by transducer 72. A surface 75 of the sound pipe 70 is oriented at an angle of 45° angle with respect to the direction of received and transmitted ultrasound energy. The surface 75 is in contact with air or another material 76 of substantially different acoustic impedance than the rigid, low sound speed material of sound pipe 70. This causes ultrasound energy to be reflected from the surface 75 by total internal reflection and to remain coherent.

A simpler version of the sound pipe is a straight section of rigid, low sound speed material that functions as a standoff for spacing an ultrasound transducer from a patient's body. The rigid nature of the sound pipe permits construction of a clip-on unit for imaging in tight quarters, e.g. a finger-tip transducer. The rigid, low sound speed material can be machined to conform to the curvature of the organ being imaged.

Several embodiments of the ultrasound-transmissive element fabricated of a rigid, low sound speed material have been shown and described above. It will be understood that the present invention encompasses any ultrasound-transmissive element fabricated of a rigid, low sound speed material. Such elements provide structural rigidity and have a sound speed that facilitates transmission of ultrasound energy to and from the human body with minimal reflection and refraction of ultrasound energy.

The present invention will be further illustrated by the following examples which are intended to be illustrative in nature and are not to be construed as limiting the scope of the invention.

EXAMPLE I

Several rigid, low sound speed polymeric compositions, for use as an ultrasound-transmissive element, were prepared using various ratios of hard and soft components. Methyl methacrylate, available from Eastman Chemical, Kingsport, Tenn., was used as the hard component in amounts between about 5.0 to about 50.0 percent, by weight. The balance of the composition was prepared with two soft components, TRIS and BIS, available from PCR, Inc., Gainesville, Fla., and Gelest, Inc., Tullytown, Pa. The TRIS ranged between about 42.5 and about 80.8 percent, by weight; the BIS ranged between about 7.5 and 14.2 percent, by weight. The monomers were mixed together after removing the respective inhibitors, and adding about 0.5 percent, by weight, AIBN initiator, available from MTM Research Chemicals, Windham, N.H. About 4.0 percent, by weight, of a crosslinking agent, neopentylglycol dimethacrylate (NPGDM), available from Dajac Labs, Trevose, Pa., was also added to provide additional mechanical strength and chemical resistance. The components and additives were mixed and cured in an oven at about 60° C. for about 12 hours the oven temperature was then increased to about 70° C. for an additional 12 hours. The resulting polymer was then allowed to cool to room temperature.

The resulting compositions were evaluated using ASTM Test No. 2240-81 to determine their Shore D durometer hardness value, as well as by time of flight to determine their sound speed. As noted above, a preferred material has a hardness of greater than about 60, and a sound speed of between about 1,450 meters/second and about 1,700 meters/second. The experimental results are shown in Table 1.

TABLE 1

| Sample | Composition (%) MMA[a] | TRIS[b] | BIS[c] | "D" Scale Hardness (Durom.) | Velocity (M/s) |
|---|---|---|---|---|---|
| 1 | 50 | 42.5 | 7.5 | 82 | 2080 |
| 2 | 40 | 51.0 | 9.0 | 78 | 1950 |

TABLE 1-continued

| | Composition (%) | | | "D" Scale Hardness | Velocity |
|---|---|---|---|---|---|
| Sample | MMA[a] | TRIS[b] | BIS[c] | (Durom.) | (M/s) |
| 3 | 30 | 59.5 | 10.5 | 73 | 1820 |
| 4 | 20 | 68.0 | 12.0 | 66 | 1700 |
| 5 | 10 | 76.5 | 13.5 | 53 | 1630 |
| 6 | 5 | 80.8 | 14.2 | 40 | 1580 |

[a]. methyl methacrylate.
[b]. tris(trimethylsiloxy)methacrylloxypropylsilane.
[c]. bis(methacryloxypropyl)tetrakis(trimethylsiloxy) disiloxane.

As indicated from the above results, the required combination of acoustic and physical properties is uncommon. Only Sample 4 has a hardness value greater than 60 D and a sound speed between about 1,450 meters/second and about 1,700 meters/second.

EXAMPLE II

Several copolymer samples were prepared, comprising various ratios of a primary component and a secondary component, and evaluated for use as an ultrasound-transmissive element. Tertbutylstyrene, available from Dajac Labs, was used as the secondary component in amounts between about 10.0 and about 25.0 percent by weight. The balance of the composition was prepared with the primary rigid component, TRIS. Samples 5, 6, and 7 used only polymerized TRIS. The compositions were prepared as described in EXAMPLE I. The experimental results are shown in Table 2.

TABLE 2

| | Composition (%) | | "D" Scale Hardness | Velocity |
|---|---|---|---|---|
| Sample | TBS[d] | TRIS | (Durom.) | (M/s) |
| 1 | 10 | 90 | 45 | 1570 |
| 2 | 15 | 85 | 60 | 1580 |
| 3 | 20 | 80 | 65 | 1660 |
| 4 | 25 | 75 | 70 | 1700 |
| 5 | 0 | 100 | 70 | 1690 |
| 6 | 0 | 100 | 70 | 1630 |
| 7 | 0 | 100 | 70 | 1615 |

[d]. tertbutyl styrene.

A wide range of the TBS/TRIS copolymers satisfied the required hardness and sound speed ranges. Samples 2 through 7 each have a hardness greater than 60 and a sound speed between 1,450 meters/second and 1,700 meters/second. Samples 2 through 4 appear acceptable for use as ultrasound-transmissive elements. Samples 5 through 7 consisted of only TRIS which appears to have good acoustic and hardness properties; the TRIS homopolymers, however, have poor machinability.

EXAMPLE III

Several copolymer samples were prepared, comprising various ratios of a primary rigid component and a secondary component, and were evaluated for use as an ultrasound-transmissive element. The compositions were prepared as described in EXAMPLE I. The experimental results are shown in Table 3.

TABLE 3

| | Composition (%) | | "D" Scale Hardness | Velocity |
|---|---|---|---|---|
| Sample | MMA | TRIS | (Durom.) | (M/s) |
| 1 | 5 | 95 | 64 | 1526 |
| 2 | 10 | 90 | 68 | 1626 |
| 3 | 20 | 80 | 75 | 1732 |
| 4 | 30 | 70 | 80 | 1880 |
| 5 | 100 | 0 | >100 | 2750 |

It is believed that even small amounts of MMA addition to the TRIS will provide enhanced machinability, allowing the copolymer to address the requirements for use as an ultrasound-transmissive element for use in the assembly of the present invention.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A medical ultrasound transducer assembly, comprising:

an ultrasound transducer for transmitting and receiving ultrasound energy; and interface means for conducting transmitted ultrasound energy from said transducer to a patient's body and for conducting received ultrasound energy from the patient's body to said transducer, said interface means comprising at least one ultrasound-transmissive element which is fabricated of a polymeric material;

wherein said polymeric material comprises at least one primary rigid component material and at least one secondary component material and has a Shore D durometer hardness value of greater than about 60D, and a sound speed of between about 1,450 meters/second and about 1,700 meters/second.

2. The medical ultrasound transducer assembly as defined in claim 1 wherein at least one said least one ultrasound-transmissive element is positioned between said ultrasound transducer and the patient's body for contact with the patient's body.

3. The medical ultrasound transducer assembly as defined in claim 1 wherein at least said one of said at least one secondary component of said polymeric material is selected from the group consisting of acrylics and styrenes.

4. The medical ultrasound transducer assembly as defined in claim 1 wherein at least one of said at least one primary rigid component of said polymeric material is selected from the group consisting of siloxanes.

5. The medical ultrasound transducer assembly as defined in claim 3 wherein at least one of said at least one secondary component is methyl methacrylate.

6. The medical ultrasound transducer assembly as defined in claim 4 wherein at least one of said at least primary rigid component is TRIS.

7. The medical ultrasound transducer assembly as defined in claim 1 wherein at least one of said at least polymeric material is copolymer of methyl methacrylate and TRIS.

8. The medical ultrasound transducer assembly as defined in claim 7 wherein said methyl methacrylate component comprises less than about 10.0 percent by weight of said copolymer.

9. The medical ultrasound transducer assembly as defined in claim 1 wherein at least one of said at least one polymeric material is copolymer of tertbutyl styrene and TRIS.

10. The medical ultrasound transducer assembly as defined in claim 9 wherein said tertbutyl styrene component comprises between about 15.0 and about 25.0 percent by weight of said copolymer.

11. The medical ultrasound transducer assembly as defined in claim 1 wherein at least one of said at least one interface means further comprises an ultrasound lens and said ultrasound-transmissive element comprises a protective cover on said ultrasound lens.

12. The medical ultrasound transducer assembly as defined in claim 1 further including means for rotating said transducer, wherein said interface means further comprises an ultrasound lens affixed to and rotating with said transducer and a fixed window positioned between said ultrasound lens and the patient's body, and wherein at least one of said at least one ultrasound-transmissive element comprises a protective cover affixed to said ultrasound lens and extending from said ultrasound lens to said window.

13. The medical ultrasound transducer assembly as defined in claim 1 further including means for rotating said transducer, wherein said interface means further comprises an ultrasound lens affixed to and rotating with said transducer and wherein at least one of said at least one ultrasound-transmissive element comprises a fixed window positioned between said ultrasound lens and the patient's body.

14. The medical ultrasound transducer assembly as defined in claim 1 wherein at least one of said at least one ultrasound-transmissive element comprises a sound pipe for coupling ultrasound energy between said transducer and the patient's body.

15. The medical ultrasound transducer assembly as defined in claim 1 wherein said ultrasound transducer comprises a plurality of transducer elements.

16. The medical ultrasound transducer assembly as defined in claim 1 further including means for rotating said transducer, wherein said interface means comprises an ultrasound lens affixed to and rotating with said transducer and a fixed window positioned between said ultrasound lens and the patient's body, and wherein at least one of said at least one ultrasound-transmissive element comprises an element of said ultrasound lens.

17. The medical ultrasound transducer assembly as defined in claim 1 wherein at least one of said at least one ultrasound-transmissive element comprises an ultrasound lens or lens element.

18. The medical ultrasound transducer assembly as defined in claim 1 wherein the acoustic impedance of said polymeric material is in a range of about 1.5 to 1.7 Mrayls.

19. A method for coupling ultrasound energy to and from a patient's body, comprising the steps of:

positioning an ultrasound transducer in proximity to a patient's body; and positioning an element between the transducer and the patient's body, said element comprising a polymeric material;

said transducer transmitting ultrasound energy to the patient's body and receiving ultrasound energy from the patient's body through said element, wherein said polymeric material comprises at least one primary rigid component material and at least one secondary component material and has a Shore D durometer hardness value of greater than about 60 D, and a sound speed of between about 1,450 meters/second and about 1,700 meters/second.

20. An element for coupling ultrasound energy to and between an ultrasound transducer and a patient's body comprising a member fabricated of a polymeric material, wherein said polymeric material comprises at least one primary rigid component material and at least one secondary component material and has a Shore D durometer hardness value of greater than about 60 D, and a sound speed of between about 1,450 meters/second and about 1,700 meters/second.

* * * * *